(12) United States Patent
Buturla et al.

(10) Patent No.: US 8,247,618 B2
(45) Date of Patent: Aug. 21, 2012

(54) OXIDATIVE DEMETALLING

(75) Inventors: Kenneth J. Buturla, Baton Rouge, LA (US); James T. Ritchie, Manassas, VA (US); Ronald D. Garton, Wezembeek-Oppem (BE); Eddy T. A. Van Driessche, Eeklo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 391 days.

(21) Appl. No.: 12/532,646

(22) PCT Filed: Mar. 31, 2008

(86) PCT No.: PCT/EP2008/053783
§ 371 (c)(1),
(2), (4) Date: Dec. 15, 2009

(87) PCT Pub. No.: WO2008/128852
PCT Pub. Date: Oct. 30, 2008

(65) Prior Publication Data
US 2010/0105944 A1    Apr. 29, 2010

Related U.S. Application Data

(60) Provisional application No. 60/925,040, filed on Apr. 18, 2007.

(51) Int. Cl.
*C07C 45/50* (2006.01)
*C07C 45/78* (2006.01)
(52) U.S. Cl. ........................ 568/451; 568/492
(58) Field of Classification Search .................. None
See application file for complete search history.

(56) References Cited

U.S. PATENT DOCUMENTS

| | | | |
|---|---|---|---|
| 3,932,523 A | 1/1976 | Strohmeyer et al. |
| 4,255,279 A | 3/1981 | Spohn et al. |
| 4,404,119 A | 9/1983 | Lagace et al. |
| 4,462,506 A | 7/1984 | Ohba |
| 4,625,067 A | 11/1986 | Hanin |
| 5,235,112 A | 8/1993 | Nadler et al. |
| 5,237,104 A | 8/1993 | Summerlin |
| 5,237,105 A | 8/1993 | Summerlin |
| 5,237,107 A | 8/1993 | Ishino et al. |
| 5,336,473 A | 8/1994 | Nadler et al. |
| 5,410,090 A | 4/1995 | Beadle et al. |
| 5,457,240 A | 10/1995 | Beadle et al. |
| 5,986,145 A | 11/1999 | Powell et al. |
| 6,331,656 B1 | 12/2001 | Blankertz et al. |
| 2004/0260113 A1 | 12/2004 | Bueschken et al. |

FOREIGN PATENT DOCUMENTS

| | | |
|---|---|---|
| DE | 199 39 491 | 8/1999 |
| DE | 102 39 134 | 8/2002 |
| EP | 0 649 851 | 4/1995 |
| WO | WO 93/24436 | 12/1993 |
| WO | WO 93/24437 | 12/1993 |
| WO | WO 01/14297 | 3/2001 |
| WO | WO 03/082788 | 10/2003 |
| WO | WO 03/082789 | 10/2003 |
| WO | WO 2006/108698 | 10/2006 |

*Primary Examiner* — Yevegeny Valenrod
(74) *Attorney, Agent, or Firm* — Andrew B. Griffis; Leandro Arechederra, III

(57) ABSTRACT

Oxidative recovery methods that use oxygen or air for recovery of homogeneous metal catalysts, such as cobalt catalysts, used in for example hydroformylation processes, can be hazardous. Explosive or flammable gas mixtures may be generated inside the process equipment, which can deflagrate upon any ignition source such as a static electricity discharge. The use of a flammable diluent has been found to be a very effective way of optimizing the recovery method, by bringing the resulting gas mixtures above their upper flammability limit. The offgas produced is then also easier to dispose of as a fuel, as compared to when a non-flammable diluent is used.

14 Claims, 2 Drawing Sheets

OXIDATIVE DEMETALLING

CROSS REFERENCE TO RELATED APPLICATIONS

This application is a 371 National Stage Application of International Application No. PCT/EP2008/053783, filed Mar. 31, 2008, which claims the benefit of US Application No. 60/925,040, filed Apr. 18, 2007, the disclosures of which are herein incorporated by reference in their entireties.

FIELD OF THE INVENTION

The present invention concerns improvements in or relating to the removal of metal compounds from the products of reactions in which the metal compounds have been used as reaction catalysts. Particularly, but not exclusively, the invention relates generally to a process of removing homogeneous metal catalyst residues by oxidation and dissolution of the oxidised metal, and is especially useful for removing dissolved cobalt compounds from the products of cobalt-catalysed carbonylation or hydroformylation reactions. This process is particularly useful in removing dissolved cobalt from crude products formed by the homogeneous cobalt-catalysed hydroformylation of olefinic feedstocks having a carbon number in the range $C_2$ to $C_{14}$, particularly $C_5$ to $C_{12}$.

BACKGROUND OF THE INVENTION

Hydroformylation reactions involve the preparation of oxygenated organic compounds by the reaction of syngas (synthesis gas), being a gas mixture that is rich in both carbon monoxide and hydrogen, with hydrocarbon compounds containing olefinic unsaturation (hereinafter "olefinic material"). The reaction is generally performed in the presence of a hydroformylation catalyst such as cobalt or rhodium, usually in a dissolved or homogeneous form, and results in the formation of a product comprising an aldehyde which has one more carbon atom in its molecular structure than the starting olefinic material. By way of example, higher alcohols useful as intermediates in the manufacture of plasticizers, detergents, solvents, synthetic lubricants, and the like, are produced commercially in the so-called Oxo Process by conversion of $C_2$ or higher olefinic material fractions (typically $C_5$-$C_{12}$) to an aldehyde-containing oxonation product having one additional carbon atom (e.g., $C_6$-$C_{13}$). Further treatment of the Oxo product by hydrogenation and distillation yields the respective alcohols. Alternatively the aldehydes may be oxidized to the respective acids.

The Oxo Process to convert olefinic material to aldehydes generally proceeds through three basic stages. These are explained below by specific reference to a cobalt catalyst, but the stages are in general also applicable to processes employing other hydroformylation catalysts.

In the first stage, the hydroformylation or oxonation reaction, the olefinic material and the proper proportions of CO and $H_2$ are reacted in the presence of a homogeneous, typically cobalt-containing hydroformylation catalyst to give a product comprising predominantly aldehydes containing one more carbon atom than the reacted olefin. Typically, alcohols, paraffins, acetals, and other species are also produced in the hydroformylation reaction. The catalytic species, in the example of cobalt, is a carbonyl species containing $Co^{-1}$ and the catalyst can be supplied to this reaction stage by numerous methods known in the art, such as by injecting an aqueous solution of a cobalt salt (such as cobalt acetate or cobalt formate) directly, or by supplying cobalt from a precarbonylation stage or catalyst makeup stage in the form of a cobalt compound already containing cobalt as $Co^{-1}$, or by supplying an organically soluble form of $Co^{+2}$, such as cobalt naphthenate, cobalt oleate, or the cobalt salt formed with heavy acid byproducts of the oxo process, or by supplying cobalt oxides, such as in a slurry. Cobalt that is supplied to the oxonation reaction in a form other than $Co^{-1}$ is then converted, under the oxonation reaction conditions, to the $Co^{-1}$ species. This conversion is also called preforming.

The oxonated organic mixture from the oxonation (or oxo) reactor(s), which typically contains various salts and molecular complexes of the metal from the catalyst (i.e., the "metal values") as well as the aldehydes, alcohols, acetals and other species, and which is conventionally referred to as the "crude oxo product" or "crude hydroformylation mixture", is treated in a second (demetalling) stage. In the demetalling stage, typically the cobalt ($Co^{-1}$) species is oxidised to the $Co^{+2}$ form, $_{and\,the\,Co}{}^{+2}$ species are then converted to a water soluble salt such as cobalt acetate or cobalt formate. The crude hydroformylation mixture is then separated into phases with the organic phase comprising the desired aldehyde (with as little as possible remaining catalyst), and the aqueous phase comprising the cobalt salt. The organic phase ("crude aldehyde") is sent to other unit operations downstream, to be converted to the desired final product. For convenience, air is often used as oxidant in the oxidation reaction. The gaseous product mixture produced by the air demetalling process will be a mixture of gases comprising possibly remaining air, hydrogen, carbon monoxide and, depending on their vapour pressure, also some of the reaction products such as aldehydes and alcohols. DE-A-19939491 discloses an oxo process where air is used for the oxidation reaction. The present invention is concerned with improving such a demetalling operation.

In a third stage the metal values removed in the second stage may be worked up in a way that they can be reused in the oxonation (first) stage. There are several ways taught in the prior art to work up this catalyst. For example, one way is to convert the aqueous metal salt to an organically miscible compound such as cobalt naphthenate, and inject it as an organic solution directly into the oxonation reactor(s). Another way is to subject the aqueous salt solution in the presence of an organic solvent to high pressure synthesis gas, converting it to active carbonyl similar to preforming, and delivering it to the oxonation stage via extraction, stripping or the like.

A more complex variation of a catalyst cycle employing an oxidation treatment is disclosed in U.S. Pat. No. 4,404,119. The process in U.S. Pat. No. 4,404,119 performs the air oxidation on an aqueous extract of $Co_2[Co(CO)_4]_2$ from the hydroformylation reaction product, after first preforming the aqueous solution to maximise the presence of the cobalt carbonyls up to its about 67%. The purpose of the oxidation step is to produce water-insoluble $Co_2(CO)_8$. The oxidation is performed optionally in the presence of an organic solvent, and the presence of CO was found to significantly improve the yield of $Co_2(CO)_8$. The oxygen-containing gas in the oxidation step of U.S. Pat. No. 4,404,119 is not introduced into the organic reaction product of a homogeneous metal-catalysed reaction.

In U.S. Pat. No. 5,986,145, an aqueous solution of 3-hydroxypropanal is contacted with oxygen to oxidise cobalt or rhodium hydroformylation catalyst species to water soluble species and byproduct carbon monoxide.

In EP 649851, the distillation residue of a hydroformylation reaction mixture containing deactivated rhodium complex catalyst is treated with a mixture of oxygen and carbon monoxide to synthesis the rhodium carbonyl compound, as the first step to synthesize the triorganophosphorus rhodium complex that is used as a catalyst in numerous processes, such as olefin hydroformylation. The carbon monoxide in EP 649851 is present as a reagent to form the rhodium carbonyl. The process of EP 649851 does not involve an aqueous phase to dissolve the oxidised metal residues and therefore is not suitable for demetalling the organic reaction product.

An improvement in the oxo process is taught in U.S. Pat. No. 4,625,067 ("Cobalt Flash Process"). The "Cobalt Flash Process" is defined as a process comprising the recovery of cobalt values from a cobalt carbonyl containing organic stream by contacting this organic stream in a stripper reactor with a stripping gas to entrain volatile cobalt compounds, in the presence of water or preferably an aqueous acid. The cobalt carbonyl containing organic stream may be crude oxo product, but in some variations may also be a cobalt performer product, or a combination thereof. A large portion of the cobalt values dissolved in such streams are in the form of cobalt carbonyl compounds, partly as dicobaltoctacarbonyl ($Co_2(CO)_8$) but primarily as hydr(id)ocobalt(tetra)carbonyl ($HCo(CO)_4$). Under stripper-reactor conditions the $Co_2(CO)_8$ disproportionates at the oil/water interface to form cobalt anions $Co(CO)_4^-$ and cobalt cations $Co^{2+}$. Under acidic conditions the cation forms a cobalt salt, and the anion forms more $HCo(CO)_4$, which may transfer again into the organic phase. The hydrocobaltcarbonyl is fairly volatile and can therefore be taken with the stripping gas overhead in the stripper reactor(s) and returned to the oxo reactor(s) by adsorption into the olefin feed stream. The acidic conditions in the stripper reactor enhance the formation of undissociated hydrocobaltcarbonyl which can be stripped. The partially decobalted crude product is then passed to the demetalling reaction and oxidised and optionally contacted with more aqueous acid as previously discussed. This oxidative demetalling reaction downstream of the stripping step removes most of the remaining cobalt traces from the organic product. This cobalt also ends up as cobalt salt in an aqueous solution, and it may be reused in the hydroformylation step, advantageously together with the cobalt salt solution from the stripper reactor, with methods such as the one set out below.

Numerous improvements and variations on the Cobalt Flash Process have been proposed, such as in U.S. Pat. Nos. 5,235,112; 5,237,104; 5,237,105; 5,336,473; 5,410,090; 5,457,240; WO 93/24437; WO 93/24436, WO 03/082788 and WO 03/082789.

In the Cobalt Flash Process, after the aqueous phase comprising cobalt formate or acetate is separated from the organic phase comprising oxo product in the demetalling reaction, the aqueous phase is passed to an evaporator where cobalt formate or acetate is concentrated before being passed to a preformer, wherein the aqueous cobalt salt ($Co^{+2}$) is converted to oil soluble $Co^{-1}$ by reaction with carbon monoxide and hydrogen, in the presence of an oil phase (commonly an aldehyde or alcohol containing stream, such as the product of the oxonation or the downstream hydrogenation reaction). Additional fresh cobalt catalyst is typically necessary and is added as, for instance, cobalt acetate.

U.S. Pat. No. 5,237,105 relates to an improvement in the process of U.S. Pat. No. 4,462,506, in that it provides a method of recovering cobalt values which does not cause the build up and recycle of unreacted light hydrocarbons within the system. It thereby avoids the need for a relative decrease in the net olefinic material feed rate in the case where a rather volatile olefinic feed material is processed. This is accomplished by providing an oxidative demetalling step prior to the stripping step. This produces an almost completely cobalt free organic hydroformylation reaction product and an aqueous product containing most or all of the cobalt as a water soluble cobalt salt. The essentially cobalt free organic phase may then be diverted for further downstream treatment, while the aqueous product containing the water soluble cobalt salt is concentrated, and the cobalt is then converted to cobalt carbonyl for reuse in a performer. The preformer effluent is then stripped to remove volatile cobalt compounds. U.S. Pat. No. 5,237,105 therefore provides a method for removing cobalt values from the crude product of a cobalt-catalyzed hydroformylation reaction formed from an olefinic material such as olefin mixtures having a carbon number in the range $C_4$-$C_{14}$ wherein an acid-air cobalt demetalling step is provided upstream of the stripping step of a Cobalt Flash hydroformylation catalyst recovery process.

The method of U.S. Pat. No. 5,237,105 comprises the steps of: (a) contacting the crude product with a stream of oxygen-containing gas, an organic acid and water, thereby producing an offgas stream, a substantially cobalt-free organic hydroformylation reaction product and an aqueous product containing water soluble cobalt salt; (b) separating the offgas and the substantially cobalt-free crude product from the aqueous product; (c) diverting the substantially cobalt-free organic hydroformylation reaction product for further downstream treatment such as distillation and/or hydrogenation; (d) concentrating the aqueous product containing the water soluble cobalt salt, thereby producing a concentrated aqueous solution of cobalt salt and a substantially cobalt-free water fraction containing a part of the organic acid, whereby the concentrated aqueous solution of cobalt salt is separated from the substantially cobalt-free water fraction containing a part of the organic acid; (e) recycling the substantially cobalt-free water fraction containing organic acid to step (a); (f) contacting the concentrated aqueous solution of cobalt salt with an alcohol stream and synthesis gas, and passing this mixture to a preforming reactor where a significant portion of the cobalt salt in the concentrated aqueous solution of cobalt salt is converted to a cobalt carbonyl; (g) contacting the preforming reactor effluent containing the cobalt carbonyl with a stream of stripping gas to entrain volatile cobalt compounds in the stripping gas and to generate, as bottoms, alcohol products and remaining dissolved cobalt salts, whereby the entrained volatile cobalt compounds are taken out overhead and the alcohol products and remaining dissolved cobalt salts are taken out as a mixed organic/water bottoms stream; (h) separating the alcohol products of step (g) from the dissolved cobalt salts; (i) recycling the alcohol products from step (h) to step (f); (j) recycling the dissolved cobalt salts from step (h) to step (a); and (k) contacting the volatile cobalt compounds from step (g) with the olefinic material; whereby the volatile cobalt compounds are absorbed into the olefinic material.

In the process of U.S. Pat. No. 5,237,105, it is preferred that the oxygen-containing gas, introduced into the system in step (a) to oxidise the $Co^{-1}$ species to the $Co^{+2}$ species, be at least one gas selected from the group consisting of: air, air with nitrogen, carbon dioxide, and mixtures of inert gases with oxygen having an oxygen content in the range of about 2 to about 10% vol. The amount of oxygen-containing gas used in the catalyst removal process of U.S. Pat. No. 5,237,105 is a function of the cobalt contained in the crude oxo product. U.S. Pat. No. 5,237,105 gives an example wherein the oxygen-containing gas is a mixture of air and nitrogen, and the nitrogen is used to dilute the mixture to about 4 volume % of $O_2$, i.e., 4.11 grams of $N_2$/gram of air. Thus, the air and nitrogen mixture is added to the crude oxo product in an amount of approximately 8.81 grams of gas mixture/gram of cobalt. Since the cobalt concentration in commercial crude oxo products is preferably in the range from about 0.05 to about 0.50 weight %, the oxygen-containing gas is typically added to the crude oxo product in an amount of from about 0.45 to about 4.50 weight %. The oxygen-containing gas is then used in a weight ratio of oxygen-containing gas relative to crude oxo product of from about 0.0045:1 to 0.45:1.

Although it is not stated in U.S. Pat. No. 5,237,105, it is believed that the nitrogen diluent is provided for safety reasons. In many hydrocarbon processing reactions and in particular those which involve the flow of hydrocarbon streams, there is a danger of electric discharge occurring inside the process equipment. In systems such as in the cobalt removal processes described in U.S. Pat. No. 4,625,067 or DE-A-19939491, which employ oxygen-containing streams, such as air, in conjunction with the hydrocarbon stream, there is a concern that the streams may combine to form a flammable and/or explosive mixture. Accordingly, in U.S. Pat. No. 5,237,105, large amounts of nitrogen are used to dilute the mixture to about 4 volume % of oxygen to render the gas non-flammable. Even if the oxygen is considered to react very quickly during normal operation, either with the cobalt or with the aldehyde in the organic stream, or the oxygen is considered trapped in small gas bubbles dispersed in the organic and/or water phase and which bubbles are considered impossible to ignite, the dilution is required as a safety measure to cover all possible scenarios, such as loss of flow of olefinic material feed and hence of liquid oxo product while the syngas keeps flowing; startup and shutdown conditions; process upsets, emergency shutdowns and emergency block-in procedures. In many of those scenarios, the oxygen could stay present for much longer, and the only gas present could be hydrogen and/or carbon monoxide, both of which have very wide flammability ranges in mixture with air.

In the process disclosed in DE-A-19939491, the flow of cobalt-containing water that circulates over the downstream three-phase settler and is recycled to the point of air injection could possibly be considered as a suitable continuous liquid phase in which to disperse the bubbles that contain the oxygen, and protect it from deflagration. However, once the three phases are separated in the settler downstream of the air injection point, the separate gas phase in the top of the settler is in continuous contact with the equipment wall. It can, therefore, in certain scenarios, still develop to an explosive mixture, and thus could possibly deflagrate upon ignition.

The separate gas phase in the top of the settler in DE-A-19939491 is relatively rich in nitrogen due to the nitrogen in the air that was injected. This poses the problem of disposal of this gas phase, typically by combustion, because the heating value of the gas is reduced by the nitrogen present.

Another concern may rise when the offgas from the oxidative decobalting step is mixed, further downstream, with off-gases from other sources that contain other flammables. In such cases, the occurrence of gas mixtures inside their flammability range should be avoided.

The need to use such a large amount of nitrogen places considerable constraints on the volumetric efficiency of the process and furthermore results in difficulties in disposal of the offgas stream from the demetalling process since of itself it has such a low heating value.

SUMMARY OF THE INVENTION

The present invention offers a solution to these problems by employing not an inert gas, but a normally flammable diluent under conditions such that the resulting gaseous mixture composition in the separate phase of the demetalling section, and downstream, is in all circumstances above the upper flammability limit of the occurring gas mixture. We have found that this counter-intuitive approach not only solves the problem, but it also enables the use of a considerably smaller amount of diluent, leading to a significant increase in the volumetric efficiency of the reaction system.

The present invention therefore provides a process for demetalling the organic reaction product of a homogeneous metal-catalysed reaction of an organic liquid, which includes the step of introducing an oxygen-containing gas into the organic reaction product to oxidise metal residues in the product, the oxidation being performed in the presence of a separate gas phase comprising flammable components, wherein said process further includes the step of introducing a flammable gas as a diluent into the separate gas phase to increase the concentration of flammables in the separate gas phase and ensure that the composition of the separate gas phase is above its upper flammability limit.

The oxidised metal residues formed in the demetalling process according to the invention typically are water soluble metal salts, which may be separated from the organic reaction product in the presence of a separate aqueous phase, preferably in the presence of an acid, such as is described herein for cobalt.

By "diluent" or "flammable diluent", we mean that the added gas, or flammable gas, "dilutes" the oxygen content of the gas phase.

One way of diluting the separate gas phase in the equipment in which the demetalling process is performed, is by introducing the flammable gaseous diluent upstream of and close to the point in the process where a separate gas phase separates out from the liquid phase(s) and due to the possible oxygen presence can comprise or develop to become an explosive mixture. As an example, in processes comprising a demetalling settler stage, the diluent gas may be added to the gas phase of the demetalling settler itself. Alternatively, it may be injected in the feed line to the settler drum. However, in this embodiment it is necessary to ensure the presence of at least one liquid phase and good mixing under all scenarios, so that pockets or stagnant zones of explosive mixtures are avoided at all times. One may not be satisfied with the protection this embodiment provides, and prefer an embodiment wherein the dilution is done further upstream. The preferred way to achieve that is to dilute the oxygen-containing gas with flammable diluent before it is brought in contact with the process stream to be demetalled. However, in such embodiment the mixing of the oxygen-containing gas with the flammable diluent poses another safety hazard. It is therefore more preferred that also the composition of this mixture should be outside its flammability range, preferably above its upper flammability limit.

The present invention therefore also provides a demetalling process for the removal of metal residues from the product of a homogeneous metal-catalysed reaction of hydrocarbons wherein oxygen-containing gas is used in the demetalling reaction and wherein a flammable gas is mixed with the oxygen-containing gas in an amount sufficient to render the composition of the mixture of the oxygen-containing gas and the flammable diluent above its upper flammability limit, and wherein the resulting mixture is then introduced into the reaction product to effect oxidation of the metal residues therein.

The invention further provides the use of a flammable gas as a gaseous diluent in a demetalling process for the removal of metal residues from the product of a homogeneous metal catalysed reaction of hydrocarbons in which an oxygen-containing gas is used in the demetalling reaction under conditions whereby a separate gas phase, present in the demetalling reaction, is brought above its upper flammability limit by dilution with the flammable gas.

In a preferred embodiment hereof, the flammable diluent is used as a diluent for the oxygen-containing gas before introduction into the demetalling reaction and the mixture of the oxygen-containing gas and the flammable diluent is also above its upper flammability limit.

In a further embodiment the invention provides an acid-oxygen cobalt demetalling process comprising contacting the crude product of homogeneous cobalt-catalysed hydroformylation of olefinic material with a stream of oxygen-containing gas, an acid and water, thereby producing an off-gas stream, a substantially cobalt-free organic hydroformylation reaction product and an aqueous product containing a water soluble cobalt salt and separating the off-gas stream from the substantially cobalt-free crude product and the aqueous product; wherein a flammable gas is used as a diluent for the offgas stream.

In a preferred embodiment, the flammable gas is used as diluent for the oxygen-containing gas before introduction into the demetalling section, in an amount sufficient to render the mixture of diluent and oxygen-containing gas above its upper flammability limit.

In another further embodiment, the invention provides another process for removing cobalt values from the crude product of a homogeneous cobalt-catalysed hydroformylation reaction, which crude product is formed from an olefinic material having a carbon number in the range C5-C9, more preferably in the range between about C5-C7, wherein an acid-oxygen cobalt demetalling step is disposed upstream of the stripping step of a Cobalt Flash hydroformylation catalyst recovery process, and a flammable gas is used as a diluent for the separate gas phase present in the acid-oxygen demetalling step and/or for the oxygen-containing gas employed in the demetalling step, under conditions that ensure that the composition(s) of the resulting gaseous mixture(s) is/are above their upper flammability level(s).

In a yet further embodiment, the invention provides another process for removing cobalt values from the crude product of a homogeneous cobalt catalysed hydroformylation reaction, which crude product is formed from an olefinic material having a carbon number in the range C5-C20, more preferably in the range between about C6-C14, wherein an acid-oxygen cobalt demetalling step is disposed downstream of the stripping step of a Cobalt Flash hydroformylation catalyst recovery process, and a flammable gas is used as a diluent for the separate gas phase present in the acid-oxygen demetalling step and/or for the oxygen-containing gas employed in the demetalling step, under conditions that ensure that the composition(s) of the resulting gaseous mixture(s) is/are above their upper flammability level(s).

DETAILED DESCRIPTION OF THE INVENTION

When small increments of a combustible gas are successively mixed with air, a concentration is finally attained in which the concentration of flammables becomes sufficient for a flame to propagate if a source of ignition is present. This is referred to as the Lower Flammable Limit (LFL) of the gas air mixture. As further increments of the combustible gas are added, a higher concentration of the flammable gas in air will finally be attained in which it then becomes the oxygen content that is too low to sustain combustion, and a flame will fail to propagate. The concentration of gas and air just as this point is reached, is referred to as the Upper Flammable Limit (UFL) of the gas in air. The conditions required for the techniques of the present invention to operate above the upper flammability limit, may be determined as follows. The explanation is given for mixtures with air, but may readily be adapted proportionally to oxygen-containing gasses having a different oxygen content, because the UFL is set by the oxygen content of the ultimate mixture.

The terms "Flammable Limit" and "Flammability Limit" are used as interchangeable throughout this document.

Below atmospheric pressure, there is no significant effect of pressure on the limits of flammability of natural gas-air mixtures and most other gas-air mixtures. From atmospheric pressure up to 2170 kPa (300 psig), the lower limit of flammability is not affected much, but the upper limit rises as the pressure of the mixture is increased. This widens the limits of flammability as the pressure increases. Formulae for calculating the pressure effects are available from literature, such as Daniel A. Crowl et al, "Chemical Process Safety, Fundamentals with Applications", Prentice Hall, N.J. 1990:

$$UFL_P = UFL_{atm} + 20.6 (\log P + 1)$$

where P is the pressure expressed in megapascals (MPa) absolute, and UFL is in vol % of fuel plus air at 1 atm. Subscripts "P" and "atm" refer respectively to the UFL of the mixture at pressure P and at atmospheric pressure.

Raising the temperature also lowers the lower flammable limit, and raises the upper flammable limit. The following equations can be used to estimate the flammable limits at an elevated temperature, expressed in t° C.:

$$\frac{LFL \text{ at } t° \text{ C.}}{LFL \text{ at } 25° \text{ C.}} = 1 - 0.000721(t - 25)$$

and $$\frac{UFL \text{ at } t° \text{ C.}}{UFL \text{ at } 25° \text{ C.}} = 1 + 0.000721(t - 25)$$

The calculation of the flammability limits of gas mixtures is carried out by the application of the mixture rule first applied in such estimations by Le Chatelier in 1891. The mixture rule is that if two limit mixtures of different gases are added together, the resulting mixture will also be a limit mixture. The empirically derived equation expressing this law is written as follows:

$$C_L = \frac{1}{\frac{Y_1}{C_{L1}} + \frac{Y_2}{C_{L2}} + \frac{Y_3}{C_{L3}} + \dots + \frac{Y_n}{C_{Ln}}}$$

Herein, $Y_1$, $Y_2$, $Y_3$ etc. are the volume fractions of each combustible gas component present in the original mixture, free from air and inerts, and so that $$Y_1 + Y_2 + Y_3 + \dots + Y_n = 1.$$

$C_{L1}$, $C_{L2}$, $C_{L3}$, etc. are the lower limits of flammability of the components in air expressed as volume fractions. $C_L$ is the lower flammability of the mixture. A similar procedure is used for determining the upper limit of flammability. It should be noted that inerts are excluded from this equation, and that at the UFL, it is the concentration of the "air" components, and thus indirectly the concentration of oxygen, that determines the flame propagation capability, although the UFL is typically expressed in terms of the concentration of the flammable components, i.e. the "non-air" components.

The flammability limits for most gasses are available from literature. For illustration purposes, those of some of the more relevant gases are shown in table 1, taken from p. 161 in Daniel A. Crowl et al, "Chemical Process Safety, Fundamentals and Applications", Prentice Hall, 1990, ISBN 0-13-129701-5. The same reference gives methods for estimating flammability limits for hydrocarbon compounds not listed.

TABLE 1

| Compound | LFL (% v in air) | UFL (% v in air) |
| --- | --- | --- |
| Hydrogen | 4.0 | 75 |
| Carbon monoxide | 12.5 | 74 |
| Methane | 5 | 15 |
| Ethane | 3.0 | 12.5 |
| Propane | 2.1 | 9.5 |
| Butane | 1.6 | 8.4 |
| Pentane | 1.5 | 7.8 |
| Hexane | 1.1 | 7.5 |
| Heptane | 1.1 | 6.7 |
| Octane | 1.0 | 6.5 |
| Ethylene | 2.7 | 36.0 |
| Propylene | 2.0 | 11.1 |
| Acetylene | 2.5 | 100 |

In view of the high UFL of hydrogen, carbon monoxide and/or acetylene, these flammable gasses are less suitable for use in the process of the present invention, and any selection from that group may therefore be excluded from the invention in a particular embodiment, because the effect obtained with any of these compounds as the flammable diluent will be much lower than with the other suitable candidates, from this list or other.

Any oxygen contained in a mixture may be considered as if it were part of the air required for combustion, and the analysis of the flammable mixture should be converted to an air-free basis before the flammable limits are calculated.

The techniques of the present invention may be used on the direct product of hydroformylation, where the cobalt concentration will be relatively high, or may be applied to the residual material present after initial removal of much of the cobalt by, for example, the cobalt flash techniques previously described. Other cobalt catalysed hydroformylation reactions are described in WO 2005/058787. The products of such a cobalt catalysed reaction include aldehydes, alcohols, oligomers, unreacted catalyst residues. After separation of the undesirable materials, such as catalyst residues which can be separated according to the present invention, the materials can be hydrogenated to produce high purity alcohols. A preferred hydrogenation reaction is described in WO 2005/058782. Alternatively the aldehydes may be optionally purified and oxidised to produce an acid, using conventional oxidation techniques. The high purity alcohols may then be used for example in the production of plasticiser esters and synthetic lubricants. Preferred esterification reactions are described in WO 2005/021482 and in our copending International Patent Applications PCT/EP001837 and PCT/EP001838 respectively. Also the acids may be esterified with an alcohol to form an ester. If the alcohol is a polyol, a polyol ester is produced. These polyol esters may also find use as synthetic lubricants. Alcohols of commercial interest may be made by esterification of the high purity alcohols made according to the invention with an acid or anhydride. The acid or anhydride preferably is selected from the group consisting of adipic acid, benzoic acid, cyclohexanoic acid, phthalic acid, cyclohexanoic dicarboxylic acid, trimellitic acid, or any of their anhydrides, or mixtures thereof.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexane equivalents, such as mono-alkyl, di-alkyl or tri-alkyl cyclohexanoates. In particular, DINP may be further hydrogenated to form di-isononyl di-cyclohexanoate (DINDCH). The process of the invention may therefore be for the production of a phthalate di-ester, in particular DINP, and further comprise the hydrogenation of the phthalate di-ester to the corresponding di-cyclohexanoate, in particular DINDCH. Suitable hydrogenation processes are disclosed in EP 1042273, US 2004/0260113, US 2006/0149097, US 2006/0166809 or WO 2004/046078.

In a further embodiment the aldehyde containing materials may be purified to isolate the aldehydes, and these may be oxidised to produce carboxylic acids, which may be used in the production of synthetic esters, which in their turn may be used as lubricants. Alternatively, the acids may be used in the production of metal salts, which find use as additives in a wide range of applications.

The present invention is particularly applicable to acid-oxygen demetalling processes which employ low molecular weight organic acids. It is however particularly suited to the demetalling processes described in our applications WO 03/082788 and WO 03/082789.

The acid used in the acid-oxygen demetalling process is used to dissolve the $Co^{+2}$ species. It is preferably a carboxylic acid, with formic acid and/or acetic acid being preferred. Formic acid may already be present as a byproduct from the hydroformylation reaction.

In accordance with the preferred embodiment of the present invention (i.e., the application of an acid-oxygen cobalt demetalling step upstream of the stripping step of a Cobalt Flash hydroformylation catalyst recovery process) an oxygen containing gas such as air, water, and an organic acid are mixed with the crude product from an oxo reactor in the acid-oxygen demetalling step described above and allowed to settle. The water stream containing a water soluble cobalt salt is thereafter separated from the now substantially cobalt-free organic hydroformylation reaction product, which is sent directly to hydrogenation thus bypassing the conventional stripping step. The water soluble cobalt salt is thereafter mixed with the water stream bottoms from the stripper reactor which also contains a cobalt salt product and these combined streams are fed to an evaporator. The evaporator concentrates the cobalt salt and generates an overhead stream of cobalt-free water and organic acid which are recycled as wash water and for use in the acid-oxygen demetalling step. The concentrated cobalt salt stream is mixed with an alcohol stream and fed to a preforming reactor where the cobalt salt is converted to cobalt carbonyls and then fed to the stripper reactor, wherein the cobalt is stripped overhead using synthesis gas and then absorbed in the feed olefinic material. The alcohol stream is preferably taken from the bottoms stream of the stripper reactor and recycled back to the preformer reactor.

Accordingly, substantially all of the organic hydroformylation product is separated from the cobalt salt aqueous product wherein the organic hydroformylation product bypasses the stripper reactor and is sent directly to a hydrogenation or distillation step. As such, the lighter hydrocarbons do not enter the stripper reactor and therefore cannot be entrained together with the volatile cobalt. Since the lighter hydrocarbons are not entrained with the volatile cobalt they cannot be absorbed into the olefinic material and thus neither build up within the catalyst recovery cycle nor do they affect the net olefinic material feed rate.

An alternative embodiment of this invention includes the application of an acid-oxygen cobalt demetalling step employing the flammable diluent, downstream of the stripping step of a Cobalt Flash hydroformylation catalyst recovery process. This embodiment is particularly useful in decobalting heavier hydrocarbons (i.e., heavier than heptene-based oxonation product). In accordance with this embodiment, crude oxonation product bypasses the acid-oxygen demetalling step and, after addition of an organic acid and water, goes directly to the stripper reactor where approximately 70% of the cobalt is stripped overhead as cobalt carbonyl using synthesis gas. The cobalt taken overhead is subsequently absorbed into the feed olefinic material or in any other suitable medium. The remaining cobalt leaves the stripper reactor as a cobalt salt via the bottoms stream. This cobalt salt along with recycled wash water is then routed to the acid-oxygen demetalling step to remove any trace levels of cobalt carbonyls. The water stream from this demetalling step is then diverted to the evaporator and concentrated. The resulting concentrated cobalt salt is thereafter mixed with a portion of the cobalt-free organic hydroformylation reaction product from the stripper bottoms stream, or an alcohol product, or recycled hydrogenation product, and fed to the preforming reactor. The preformer product is mixed with the oxonation product and fed to the stripper reactor.

Accordingly, cobalt values are removed from the crude oxo product of a cobalt catalyzed hydroformylation reaction by contacting the crude product with a stream of stripping gas to entrain volatile cobalt compounds and the contacting is performed in the presence of water and organic acid to dissolve those cobalt values not entrained in the gas under the conditions of temperature and pressure employed for the contacting.

The stripping gas which is preferably used in accordance with this invention is synthesis gas (i.e., a gas mixture rich in carbon monoxide and hydrogen). The particular proportions of the two components in the synthesis gas are adjusted to suit the reaction system.

The stripping reactor preferably operates at relatively low pressures, i.e., pressures lower than the decomposition pressure of the cobalt compounds present in the crude hydroformylation reaction product at the temperature conditions employed. More preferably the pressure is below 20 bar absolute, most preferably below 10 bar, especially for example a low pressure below 7 bar such as from 1 to 5 bar absolute. The temperature employed generally relates to the pressure and is preferably less than or no more than 100° C., or 90° C., more preferably from 60°-100° C., especially 60° to 80°, 85° or 90° C. The temperature in the stripper bottoms is preferably between about 88° C. and about 93° C.

In accordance with either mode of operation, the demetalling step is preferably followed by a preformer reactor. The concentrated cobalt salt is preferably introduced into the cobalt preformer, and the resulting mixture of water, gas and organics may be injected into the oxo reactor, or into the crude oxo product downstream of the oxo reactor but upstream of the stripper reactor, or directly into the stripper reactor. Here the stripping gas carries off the volatile cobalt carbonyls (including those newly introduced to the system from the cobalt preformer) and, via absorption into the olefinic feed material, they are recycled into the oxo reactor. By such an embodiment only minimal quantities of fresh cobalt need to be introduced into the oxo reactor, as make up for an otherwise closed system.

The preformer reaction that results in the formation of cobalt carbonyl compounds is conveniently promoted with a noble metal catalyst, in particular a catalyst selected from the metals in Group IB and in Group VIII of the Periodic Table. Such promotion catalysts are preferably heterogeneous.

Representative examples of useful catalyst material include gold, platinum and palladium. Palladium is the preferred catalyst metal. Preferably, the active catalyst materials are embedded on a solid support such as carbon, coke or alumina. Typically, when a supported catalyst system is used, the active catalyst metal makes up approximately 0.1 to 5.0 weight percent, preferably 0.2 to 2.0 weight percent of the total supported catalyst structure.

The olefinic material that is hydroformylated may be short or long chained compounds containing olefinic unsaturation, depending on the final product desired. Most organic compounds possessing at least one non-aromatic carbon-carbon double bond may be reacted by this method. Generally the compound will have at least three carbon atoms although hydroformylation using ethylene is known (see, for instance, U.S. Pat. No. 6,150,322). Thus, straight and branched-chained olefins and diolefins such as propylene, butylenes, pentenes, hexenes, heptenes, octenes, nonenes, decenes, undecenes, dodecenes, tridecenes and tetradecenes, butadiene, pentadiene, styrene, olefin oligomers such as di- and tri-isobutylene and hexene and heptene dimers, olefinic fractions from the hydrocarbon synthesis process, thermal or catalytic cracking operations, and other sources of hydrocarbon fractions containing olefins, and mixtures of all of these, may be used as starting material, depending upon the nature of the final product desired. The feed may include a mixture of isomers, both skeletal and in double bond location or it may be isomerically pure (or nearly so) skeletally and/or in double bond location.

In a preferred embodiment, the olefinic material is a mixture of olefins having a carbon number of from $C_3$ to $C_{18}$, more preferably $C_5$ to $C_{18}$. It will be recognized that the olefin feed may not consist of 100% olefins, nor of 100% olefins within the specified carbon number range, but may be a distribution of olefins having different carbon chain lengths. In a particularly preferred version of this embodiment at least 50 wt. %, preferably 70 wt. %, more preferably 80 wt. %, still more preferably 90 wt. % of olefins are in the specified carbon number range. In certain cases it may be preferable to use a feed of 100 wt. % (or nearly so) of the specified carbon number or carbon number range.

In another preferred embodiment, the olefinic material is the olefinic reaction product of the acid catalyzed oligomerisation of propylene and/or butenes, which may also optionally also include pentenes.

In yet another preferred embodiment, the olefinic material is the olefinic reaction product of the oligomerisation of various olefins and compounds having olefinic unsaturation, using regular or surface deactivated zeolite catalysts as described in U.S. Pat. Nos. 3,960,978; 4,021,502; 4,076,842; 4,150,062; 4,211,640; 4,520,221; 4,522,929; 4,524,232; 4,547,613; 4,568,786; 4,855,527; 4,870,038; 5,026,933; 5,112,519; 5,245,072; 5,417,869; 5,985,804; and 6,013,851.

Even more preferred as olefinic material in the present invention are $C_6$ to $C_{26}$ olefins, such as $C_8$ to $C_{26}$ olefins, more preferably $C_8$ to $C_{23}$ olefins, most preferably $C_8$ to $C_{18}$ olefins, conveniently prepared by contacting lower olefins under polymerization conditions with siliceous monodimensional acidic zeolites such as ZSM-22 and ZSM-23 zeolite having pore activity and wherein the zeolite surface is rendered substantially inactive for acidic reactions. By "lower olefins" or "lower olefinic material" as used herein is simply meant that the starting material to be oligomerised over the zeolite has lower carbon numbers than the final product. The oligomers may be dimers, trimers, tetramers or higher oligomers, or mixtures thereof. It is preferred that the starting material is a $C_3$ or greater olefin (or mixtures thereof), and in a preferred embodiment the olefinic material supplied to the oxonation reactor(s) according to the present invention derive from the oligomerisation of $C_3$ and/or $C_4$ olefins using the aforementioned modified zeolites. In a particularly preferred embodiment, a feed is used comprising butenes (more preferably n-butene) and propylene in the ratio of about 1:0.01 to 1:0.049 wt%. Conveniently, paraffins are also present in the feed to act as a heat sink in the reaction. The amount of paraffins to use can be determined by one of ordinary skill in the art.

In another embodiment the process of the invention uses LAOs and/or LIOs (linear alpha olefins and linear internal olefins, respectively), which terms are well-known in the art, as olefinic material.

Other olefinic materials that may be used as a feed into the oxonation reactors include oligomers produced by the Octol® process or the Dimersol® process. See, for instance, the previously mentioned U.S. Pat. No. 6,015,928. Octol® and Dimersol® are registered trademarks owned respectively by Degussa and Institut Français du Pérole (IFP). Other preferred olefinic materials may be made using the process as described in U.S. Pat. No. 6,437,170. Yet other olefinic materials include oligomers produced using solid phosphoric acid (SPA) catalysts and those produced using ZSM-57 catalysts, procedures which are known in the art. Other olefinic materials may be produced using oligomerisation processes as disclosed in WO 2006/133908, WO 2006/133967 or WO 2007/006398.

An alternative feed comprises 0.1-20 wt % isoolefin, particularly isobutylene and/or isoamylene, more preferably wherein the content of the isobutylene and/or isoamylene is from 0.5-5.0 wt %. A preferred source of such a feed is the unreacted effluent from a methyl tertiary butyl ether (MTBE) unit.

Typical hydroformylation reaction conditions include a temperature of about 125° C. to about 200° C. and/or a pressure of about 100 bar to about 350 bar, and/or a catalyst to olefin ratio of about 1:10000 to about 1:1. The molar ratio of hydrogen to carbon monoxide is conveniently in the range of about 1 to about 10. The process may also be carried out in the presence of an inert solvent such as a ketone, e.g., acetone, or an aromatic compound such as benzene, toluene or xylenes.

One aspect of the present invention is separating the decobalted distillate or condensate generated in the evaporator step (step (d) in the Cobalt Flash Process set forth above), in the case acetic acid is used, into an acetic acid-depleted water stream, preferably to be recycled as aldehyde product wash water as described in more detail below, and an acetic acid-rich stream, preferably to be recycled as process make-up acid, e.g., to the stripper reactor(s) and/or to the demetalling stage.

The acetic acid-rich portion from the separation step may be recycled into the process at any desired point, preferably in the demetalling reactor(s) and/or in the stripper reactor(s).

The acetic acid-depleted water stream can be used as desired. In a preferred embodiment, the acetic acid-depleted water stream from the condensate separation step is used in a wash tower to wash the organic phase containing crude aldehyde product from the demetalling reactor(s). In this preferred embodiment, decobalted oxonation product from the demetalling reactor(s), which still contains some acetic acid and other water-soluble impurities, is washed with the water from the aforementioned evaporator condensate separation step. The thus-washed oxonation product is passed overhead from the wash tower to the next desired processing step, such as hydrogenation or further oxidation. The wash water, now more concentrated with acetic acid extracted from the organic phase, is taken off as bottoms. This dilute acetic acid may now be used directly in the process as desired, such as in the demetalling reactor and/or in the stripper reactor(s). By this preferred embodiment of using the internal process fluids to wash the organic phase comprising the aldehyde, the purity of the desired product is significantly improved and additional economic advantages are achieved by more complete and efficient acetic acid recycle.

In one embodiment according to the invention, the or more than one of the hydroformylation reactors may be partitioned into a plurality of successive adiabatic beds. The temperature of these beds may be controlled by injection of a colder cooling liquid in between the beds. Inside the same reactor, these beds may be separated by baffles. Such a partitioned reactor may be positioned vertically with the reaction mixture flowing upwards from one bed to the following bed. This is preferred because of the two-phase vapour/liquid nature of the reaction mixture. In this arrangement the baffles may be termed bed decks. Such reactors are preferably cylindrical, and the bed decks preferably have a centre hole for passing the reaction mixture, which may extend upwardly into the downstream bed by means of a short vertical conduit or pipe. This pipe section provides a preferred volume for mixing the hot outlet of the upstream bed with the colder cooling liquid injected for temperature control. The cooling liquid is therefore preferably injected immediately below, and thus upstream, of the vertical pipe section. The vertical pipe section may also be provided with internal baffles, such as disk and donut shapes, to enhance mixing of the cooling liquid with the reaction mixture. Excessive turbulence in this mixing zone is however preferably avoided, because this may create local pressure drops, such that the partial pressure of carbon monoxide may become lower than what is needed for stability of the carbonyl catalyst, especially cobalt carbonyl. This may cause the catalyst to start clustering and come out of solution as solid clusters and even as cobalt metal. This may deposit on the reactor internals, in particular on the internals of the vertical pipe, and may ultimately lead to flow obstruction.

In the downstream bed, at a distance above the vertical pipe, there may be provided means for forcing the fluid flowing through the pipe to change direction, preferably from axial to radial relative to the reactor, such that the volume of the bed is used efficiently. In order to reduce the risk of having stagnant zones in the bed, these means for forcing the change of flow direction may be a baffle, preferably a horizontal baffle. It is even more preferred to provide a baffle that, between the vertical pipe and the vertical walls of the reactor bed, extends downwards to force fluid flow back down. We prefer to use a baffle that is curved downwards at the outer ends, towards the bed deck, such that the assembly of vertical pipe and baffle resemble the shape of a mushroom stem and cap. The fluid flow coming from the vertical pipe is then forced to spread radially from the centre to the perimeter of the cross-section of the bed, at the same time directing the fluid flow down towards the bed deck. In order to avoid a stagnant vapour space collecting under the mushroom cap, we prefer to provide perforations in the curved baffle.

As cooling liquid for controlling reactor and bed temperatures, we prefer to use part of the reactor liquid effluent, or the liquid effluent from a reactor stage that comprises more than one reactor, which has been cooled before injection. We therefore prefer to pass the reactor effluent through a hot gas separator, wherein a portion of the liquid is withdrawn from the rest of the reactor effluent. These hot gas separators may be simple drums without instrumentation, because the overhead stream is still two phase. The withdrawn liquid is then preferably cooled in interstage coolers and pumped by cooling liquid pumps, or booster pumps, into the hydroformylation reactor. If gasses are still present after cooling, the cooled withdrawn liquid may be passed through a cooling liquid separator, such that there is less risk of passing gas to the cooling liquid pumps. This cooling liquid separator may be provided with a level control device. The gas separated may be reused by a gas consumer at lower pressure, such as a downstream oxo reactor, or be compressed, e.g. for recycle.

The interstage coolers may be provided with static devices to increase turbulence in order to improve the heat transfer coefficient at the process side. However, catalyst stability is preferably preserved, and these devices may therefore preferably only be provided in those places where the withdrawn liquid is not anymore at the temperature of the hot gas separator. We prefer to use double helix static mixer inserts inside the heat exchanger tubes, but any other suitable design can be used. If the interstage coolers are provided as two or more coolers in series, we prefer to only provide devices to increase turbulence in the coolers downstream from the lead cooling liquid cooler. Increased turbulence may increase heat transfer, and improved heat removal may improve the operating stability and equipment productivity.

In a reactor system having a plurality of reactors cooled with cooling liquid recycle, these cooling liquid circuits may be interconnected to provide flexibility for redistributing reaction loads from one reactor or reactor stage to another, either in between parallel trains of reactors, or between reactors in series with each other or in a different position in a parallel train. This is particularly useful when these reactors are pushed to their ultimate capabilities, also because reactor control may then have become more difficult. Another option to push throughput is to add olefin to the cooling liquid before injection into the reactor, especially reactors or reactor beds not in the lead position, because these may have extra heat removal capacity while the lead reactor may already be limited. This may bring extra cooling to that reactor stage but at the same time add to the amount of olefin that is being processed overall.

Such multibed reactors cooled with recycle cooling liquid, especially when several are in provided in parallel and or series, in particular when these reactors or their beds are not uniform in size, may become very difficult to control, particularly when operating at high throughput. In addition, partial olefin and/or syngas bypass over lead reactors into downstream reactors may be added in order to unload some of the lead reactor duty and keep them operating in a hydraulically but even more importantly a thermally stable regime. We have found that, for control of complex reactors such as described, particularly their temperature control, in complex reactor schemes such as described, a high level dynamic matrix control (DMC) system including feed forward prediction mechanisms in a multivariable environment is particularly useful. Such a control system monitors all constraints and constantly tries to advance the operations toward the next constraint.

We have also found that pressure control is important in operating a hydroformylation reaction. We have found it advantageous to control the syngas supply pressure to the hydroformylation reactor by controlling the inlet pressure to the high pressure (HP) compressors. This allows the reactor pressure to be kept as high as possible. We have found that this control is preferably done by controlling a recycle flow of intermediate pressure (IP) offgas from downstream to the HP compressor. This IP offgas is separated from hydroformylation reactor product, optionally but preferentially after cooling the reactor product, separating excess gas from the reactor outlet in a high pressure separator, and letting the liquid from this separator down to a lower pressure. This pressure let down may also be done in a plurality of steps, and each step may then result in an IP offgas, usually at different pressures. These offgasses will have different compositions, due to differences in vapour/liquid equilibria for the individual stream components. Depending on their composition, there may be preferences for purging one or a selection of those streams, if only partially, and preferably recycling more of the other offgas stream or streams. In many cases it is more desirable to purge IP offgasses than HP offgasses, to control the buildup of inerts in the gas system around hydroformylation. This is particularly true for control of inerts such as methane and carbon dioxide, but may be less desirable to control nitrogen. Suitable purge and recycle schemes are also disclosed in WO 2005058787, which is hereby incorporated herein.

When different feed olefin qualities are to be processed, and cross contamination of the respective products is to be limited, there may be an inert fluid flush applied between the processing of the two olefin qualities, as part of the grade switch procedure. We have found that the light oxonation fraction (LOF), i.e. the mixture of unreacted olefins and paraffins from the hydroformylation reaction, optionally combined with those from the downstream hydrogenation reaction, which is typically separated from the product aldehyde and/or alcohol in a distillation tower, is particularly suitable for use in such inert fluid flush, because it is substantially inert and, if chosen correctly, readily separable from the desired products. This inert fluid flush affects the heat balance of the reactors, requiring adjustment of temperature control settings and cooling liquid flows and flow alignments. The cooling liquid alignment control also helps in minimizing cross-contamination between the two consecutive grades. We have found that the DMC system is particularly suitable to control these adjustments.

For smooth operations of the catalyst cycle, and thus of the Oxo reactor section, it is important to analyse the catalyst concentration in certain streams accurately and frequently, preferably by at-line analysis (i.e. manual analysis performed in or close to the unit), but more preferably by on-line analysis. Such streams are e.g. the cobalt-containing olefin to the reactor section and/or the concentrated $Co^{2+}$ solution to be subsequently preformed as cobalt catalyst make-up. Multi-stream on-line analysers are particularly advantageous. We have found that for this purpose, a multi-stream on-line X-Ray Fluorescence-based cobalt analyser is particularly suitable.

The crude aldehyde product of the invention, preferably after washing for removing traces of catalyst and remaining acid from the demetalling step, is typically hydrogenated to produce a hydro product. Typically such hydrogenation employs a heterogeneous catalyst and many types of catalysts are suitable. WO 2005058782 discloses suitable hydrogenation catalysts and processes. In addition, we have found a sulphided cobalt/molybdenum catalyst to be particularly suitable in this service. Also particularly suitable are the reduced nickel-molybdenum catalysts, e.g. carried on alumina support, that are disclosed in X. Wang et al, "Characterization of Active Sites over Reduced Ni—Mo/$Al_2O_3$ Catalysts for Hydrogenation of Linear Aldehydes", J. Phys. Chem. B 2005, 109, 1882-1890, which catalysts we have found are also suitable for hydrogenation for branched aldehydes. These catalysts preferably contain no, or only small amounts of phosphorus, such as 0-1.0 wt % P, more preferably 0-0.5 wt % P, as disclosed in U.S. Pat. No. 5,382,71. Most preferably they are substantially free of phosphorus, as disclosed in U.S. Pat. No. 5,399,793.

Many types of fixed bed reactors are suitable for hydrogenation services. Tubular reactors are particularly suitable because of their temperature control advantages, but adiabatic chamber reactors may also be used. Such chamber reactors may contain a plurality of beds, and bed temperatures may be controlled by interbed quench, either by cooled recycle liquid or cooled hydrogen injection, fresh and/or recycled, into quench zones in between catalyst beds. It is important to mix the colder quench with the hot bed effluent well before entering the downstream bed. Therefore distributors and/or quench boxes may be provided. However, these reactor internals may impair easy catalyst unloading when it is deactivated, and/or make the loading of fresh catalyst more difficult. We have found it advantageous to provide a special reactor internal, called a removable quench box, such that it is readily removed during a catalyst changeout and replaced afterwards.

Such a removable quench box is now described for a downflow reactor, where it is placed in between two catalyst beds. Along the perimeter of the reactor cross section, at a suitable height between the two beds, are provided a number of lugs, welded to the reactor wall, protruding a distance towards the centre of the reactor, but leaving a free diameter, $D_L$, available for passage between the lugs. We prefer to provide at least 6, preferably at least 8, more preferably at least 12 lugs around the perimeter of the reactor cross-section, all at the same height and preferably about evenly distributed over that perimeter. After the catalyst for the lower bed is loaded and its top surface evened, a ring is placed on the lugs to provide a circular support ledge along the reactor wall, to support the quench box. For ease of introduction into the vessel, this ring preferably consists of at least two segments which together cover the entire perimeter of the cross section. Such a segmented ring may be called a split ring. The outer diameter of the split ring preferably fits closely to the reactor wall. The inner diameter of the split ring, labelled $D_R$, must be smaller than $D_L$ defined above.

The quench box has the outer shape of a short cylinder, of which the outer diameter is smaller than $D_R$, but which is provided with a side rim having an outer diameter that is larger than $D_R$ but smaller than $D_L$. As such, the quench box is able to pass the lugs that are provided for upstream quench boxes in the same reactor, but finds good support with its side rim on the split ring provided for this particular quench box. We prefer to provide the side rim of the quench box close to the upper surface of the short cylinder shape of the quench box. A sealing material, such as an asbestos rope, may then be stuffed around the entire perimeter between the reactor wall and the rim of the quench box, minimising the fluid bypassing the quench box along the reactor wall. The sealing material may then be retained in place by another segmented retainer ring placed on top of the quench box along the wall of the reactor vessel on top of this sealing material, and fixed to the quench box.

The quench box itself may internally have one or more vertical sections, separated by horizontal plates. We prefer to provide three sections, the top section for introducing the quench fluid or cooling fluid, the middle section for intimately mixing the two fluids, and the bottom section for properly distributing the mixed fluid over the downstream catalyst bed. The top layer of the quench box assembly conveniently is a support grid and catalyst screen for the upper catalyst bed. We prefer this support grid to extend beyond the quench box side walls, thereby conveniently forming the side rim having the diameter within the limits as described above, such that the bed support grid finds direct support on the split ring.

Through the catalyst screen and bed support grid, the fluid leaving the upper bed is allowed to enter the top section of the quench box. This top section, below the bed support grid, preferably is a section for introducing and distributing the cooling fluid to control the temperature into the downstream bed. Any conventional type of tube and nozzle arrangement may be suitable, though it is preferred to provide a plurality of nozzles, such as 3, 4, 5, 6 or 7 nozzles, the more the better, distributed as evenly as practical over the cross section of the quench box.

As middle section of the quench box, we prefer to provide one or more mixing zones, which together provide for intimate mixing between the effluent from the upper bed and the cooling fluid that was introduced into the quench box top section. We prefer to provide two mixing zones. We prefer that the fluid from the top section enters the first mixing zone through one centre opening provided in the first horizontal plate, and is then forced by a second horizontal plate to flow radially outwards, towards the outer vertical wall of the quench box. Along this radial flow path, the fluid may be further forced to swirl and mix with the help of any conventional type of mixer or baffle assembly. In this mixing zone, flow turbulence is still highly desirable. Because of the two phase flow however, we have found it important to provide perforations or slots into such baffles, so that the formation of stagnant vapour or liquid zones is avoided.

The reactor fluid may then conveniently leave the first mixing zone and enter into a second mixing zone, through openings suitably provided close to the perimeter of the second horizontal plate. On the bottom of this second horizontal plate, we prefer to have notched pipes welded to the bottom of these openings, with notches oriented to provide cyclonic flow. These multiple cyclonic fluid flows are released onto a third horizontal plate, conveniently provided with one or more openings having preferably a large diameter to slow down the fluid velocity, and through which the fluid leaves the second mixing zone, and thereby leaves the middle section of the quench box to enter into the bottom section of the quench box. We prefer to have one of such openings in the centre of the third horizontal plate, such that the fluid flow in this second mixing zone is forced radially inwards with respect to the quench box axis. Because flow turbulence in this last mixing zone above the quench box bottom section may be less desirable, we prefer to have no more mixers and/or baffles in this zone.

As bottom section of the quench box, we prefer to provide a two-phase flow distributor to distribute the reactor fluid over the top surface of the lower bed. Any conventional type of distributor tray may be suitable, and we prefer to use a tube and slotted chimney assembly.

The quench box may further conveniently be provided with thermowells, as well as with penetrations through the box as needed to provide guides for thermowells that may desirably be provided to any thermocouples in lower reactor sections. Penetrations may also be provided for piping to bring cooling fluid into the quench box, or connect to piping that bring cooling fluid into another quench box that may be located further down the reactor. To minimize fluid bypassing, each penetration is preferably sealed, such as with a packing gland that may be tightened from above the quench box assembly.

We have found that this quench box assembly minimizes the work required inside the reactor during catalyst changeout, and hence minimizes reactor down time as well as the chance for assembly error that could lead to fluid maldistribution. The assembly activity is limited to (i) placing the split rings on the support lugs, (ii) lowering the quench box with its side rim onto the split ring, (iii) providing packing material in the gap between the reactor wall and the quench box, and securing this packing material in place with the retainer split ring, and (iv) making all internal connections for the cooling fluid piping, the thermowells and/or the thermowell guides, and tightening the packing glands.

When a sulphided hydrogenation catalyst, such as cobalt/molybdenum or nickel/molybdenum, is used, it may be pre-sulphided and activated before loading and loaded in a fully active state; or it may be pretreated with a sulphiding agent and activated in situ after loading into the reactor; or it may be loaded as an oxide precursor and be sulphided and/or reduced in situ. We prefer to sulphide the metal oxide catalyst precursor in situ up to 332-337° C. (630-640° F.). at low pressures such as 450-800 kPa (50-100 psig), and using a sour gas such as a mixture containing hydrogen and at least one sulphur component such as $H_2S$, DMDS and/or a DMDS decomposition product. However, these conditions may differ for different mixed metal oxide catalysts, e.g. Ni/W is easier to sulphide than Ni/Mo, and Co/Mo is in between. More details may be found in the disclosure already mentioned, by X. Wang et al, "Characterization of Active Sites over Reduced Ni—Mo/$Al_2O_3$ Catalysts for Hydrogenation of Linear Aldehydes", J. Phys. Chem. B 2005, 109, 1882-1890.

The hydro(genation) product may contain carboxylic acids having the same carbon number as the alcohol, typically in small quantities. These may be formed by various side reactions occurring upstream, and are difficult to remove in the hydrogenation step. They are unwanted because of their corrosion potential. These acids are particularly less desired in the distillation operation that typically distils the product alcohol from the lighter and heavier fractions that are still present in the hydro product. After distillation, these fractions may be designated as LOF (light oxonation fraction) and HOF (heavy oxonation fraction). The acids, under distillation conditions and in particularly in the product alcohol fractionator, may react with alcohol to form di-alkyl esters and water. The esters end up in the HOF, and the water typically goes overhead with the product alcohol, where it is considered a contaminant that may have to be removed if present in concentrations above what the product specification allows. We have found that it may be advantageous to treat the hydro product stream with a dilute alkaline solution before it is sent to distillation, preferably by dilute sodium hydroxide or caustic. When dilute caustic is used, we have found it advantageous to select the dosing and concentrations such that the formation of sodium carbonate is minimised in favour of sodium bicarbonate. This is because sodium carbonate is less soluble, and may cause fouling and plugging downstream. This treatment not only reduces the acidity of the hydro product stream, but may also hydrolyse remaining formate ester. It also significantly reduces corrosion in the downstream distillation unit. The spent alkaline solution from this treatment contains acid values and these may be recovered as the stream may be reused in the cobalt catalyst cycle, preferably in the step where the water soluble organic cobalt salts are converted to organic soluble cobalt salts.

Formate esters are known byproducts formed in hydroformylation. In the downstream hydrogenation unit, these formate esters are known to decompose, in the presence of water, and partially form carbon dioxide. This carbon dioxide is fairly soluble in the hydro product. When the hydro product is treated with a dilute alkaline solution as explained above, the carbon dioxide consumes part of the base. The presence of carbon dioxide in the hydro product therefore increases the consumption of base in the treatment step. We therefore prefer to remove carbon dioxide from the hydro product before the alkaline treatment step. This may be accomplished by stripping the hydro product with a gas, for example. We prefer to achieve this by bubbling gas through the low pressure separator provided in the back-end of the hydrogenation step. We prefer to use a combustible gas, such as methane or natural gas, so that the spent gas may still be valuable as a combustible. In addition, we prefer to have a small stripping tower on top of this low pressure separator, and feed the hydro product to the top of this stripping tower. We have found that with two stripping stages, most of the carbon dioxide can be stripped from the hydro product. The offgas from the stripping tower may be used, e.g. as a fuel, such as to fire a furnace.

Treating the hydrogenation or "hydro" product with an alkaline solution to reduce carboxylic acids present, may lead to organic salts being present in the distillation feed. These typically end up in the HOF byproduct. These salts are not a problem, but on the contrary an advantage, when the HOF is reused as a cobalt catalyst carrier, i.e. as an organic solvent for an organic soluble salt of $Co^{2+}$. They may be less desired in other applications, such as when the HOF is combusted, or used as catalytic cracker or steamcracker feedstock. We therefore find it useful to submit at least part of the HOF byproduct to a desalter operation. We prefer to use a 2-stage desalter step, where the HOF is first treated with water, e.g. demineralised water or boiler feed water, and in a second step with a dilute water soluble organic acid solution, preferably formic or even more preferably acetic acid. Each step preferably uses a direct current (DC) electrostatic grid for assisting the phase coalescence after the mixing, and is followed by a settler to remove water soluble salts in the water phase. The first step may only be a physical wash, or may also use some of the spent alkali solution from the upstream treatment of the hydro product. In the second step, the heavy organic salts are converted to lighter organic salts that are more water soluble. We have found that sodium levels of the order of 3000-6000, optionally up to 7000 and even up to 18000 ppm by weight in the HOF may readily be treated, and that the sodium content may be reduced to 200 ppm or below, preferably 50 ppm or below, more preferably down to 20-40 ppm. Even sodium contents as low as 1-5 ppm by weight may be achieved with such a desalter setup. The water soluble organic acid is important in achieving effective HOF desalting.

Another aspect of the present invention is controlling the accumulation of formic acid in the process by flowing alcohol through the preforming section, and allowing the alcohol to selectively react with the formic acid, whereby the resulting formate ester can be removed from the system in the demetalling stage due to the formate esters' solubility in the product aldehyde. The formate ester can be subsequently removed from the final product, for instance by decomposition during hydrogenation. This aspect of the present invention will be described in more detail below.

The source of the organic alcohol to the preformer may be, for instance, a portion of the final alcohol produced by hydrogenation of the aldehyde. The organic alcohol may also come from using a portion of the crude aldehyde product of the oxonation reaction, particularly before but optionally after it has been washed to remove formic and/or acetic acid, such as in accordance with the aspect of the present invention discussed previously (i.e., oxonation reaction produces some alcohol, which gets passed through with the organic phase in the wash tower). The organic alcohol may also come from using a portion of the hydrogenation product. The actual source of organic alcohol used in the preformer is per se not critical for the purpose of removing formic acid; it may be, for instance, that an alcohol other than product alcohol is preferred, depending on the circumstances. Overall process optimization, however, may depend on using internal process fluids, i.e., unwashed or washed crude aldehyde, hydro product, or final product alcohol, as the organic alcohol used in the preformer.

The material from the preformer is then passed into the stripper reactor(s) to complete the recycling of the cobalt values. The formate ester formed in the preformer is removed from the system with the organic phase in the demetalling step.

We have found that there are advantages to bringing preformed cobalt to the hydroformylation reactors, as compared to bringing $Co^{2+}$ to the hydroformylation reactors and preforming this into $Co^{-1}$ in those reactors. The processes without preforming in the hydroformylation reactors are particularly tolerant to feeds containing dienes, more particularly conjugated dienes. We have found that these processes are able to process feeds with significant amounts of dienes, even conjugated dienes. We have found that such processes are able to process feeds containing dienes at concentrations up to 5% wt, such as C5 raffinate streams from isoprene extraction units, of which the typical olefin content is around 50% wt, and diene levels may be as high as 3 or even 3.5% wt. On higher molecular weight streams, this acceptable diene level is even higher. We have found that those processes wherein the cobalt catalyst needs to be converted to its active carbonyl form in the presence of its olefin feedstock, are impaired when dienes are present in the feedstock. This is because the dienes, particularly conjugated dienes, appear to significantly reduce the so-called cobalt preforming reaction, wherein cobalt is converted from its starting compound, such as cobalt oxide or cobalt salt such as formate, acetate, or an oil soluble salt such as e.g. oleate, to its active carbonyl form. In those more sensitive hydroformylation processes, we prefer to operate with an amount of dienes in the feed that is not higher, on a stoichiometric basis, than the amount of cobalt that is fed to the hydroformylation reaction. We therefore prefer the dienes in the feed to these diene sensitive processes to be at most at the same molar level as the amount of cobalt in the feed, preferably at most 0.2 times, more preferably at most 0.1 times the molar amount of the cobalt in the feed.

The normally flammable diluent that is used according to the present invention may be any suitable combustible material. Less suitable are those compounds that can undergo exothermic reactions even in the absence of oxygen and have an upper explosion limit of 100%, such as acetylene and ethylene oxide. Also, those compounds having a relatively high UFL, such as carbon monoxide with an UFL of 74% vol in air, are less favoured. Preferred are those compounds that have a lower UFL than hydrogen and are compatible with the process, such as by virtue of being not reactive under the prevailing conditions with any of the other compounds already present, and by virtue of not interfering with any of the process steps. Examples of materials that can be used advantageously include methane, natural gas, and hydrocarbon containing diluents, and we have found that when such diluents are used, satisfactory reaction conditions and metal recovery may be achieved with considerably less diluent than when nitrogen is used as the diluent. This enables a safe process with more efficient reaction conditions and overcomes the hazardous situation that can arise if oxygen-containing gasses are used for demetalling without the use of a diluent.

The present invention is illustrated by reference to the following example which compares the present invention with the process of U.S. Pat. No. 5,237,105. The example uses air as the oxygen-containing gas, but may be adapted proportionally to an oxygen-containing gas having a different oxygen content, as explained above. The example uses methane as the flammable gaseous diluent, but the equivalent with any other flammable gaseous diluents is easily determined. It should be noted that the amount of diluent required will depend on the type of diluent used and the UFL thereof. Paraffinic hydrocarbons in general are preferred diluents, because of their very low UFL and their relative inertness to the process. Paraffinic gases with a lower UFL than methane would be even more effective than methane in lowering the mixture UFL, but as they are typically also less volatile, they pose a higher risk of interference with the process. Hence, and also thanks to its availability and low cost, methane and/or natural gas are attractive candidates for the flammable diluent to be used in the process according to the invention.

In the process of U.S. Pat. No. 5,237,105, to ensure that the operation stays outside the flammable range, a large nitrogen flow is added to the air stream to reduce the oxygen content below 5 vol % thereby making the gas mixture too oxygen-lean to burn when mixed with hydrogen. The basis for determining the required nitrogen addition rate assumes a pure hydrogen and/or carbon monoxide environment, with an upper flammable limit (UFL) of 75 vol % and 74 vol % respectively, into which the air-nitrogen stream will be mixed. The oxygen content limitation requires a nitrogen flow of 4 to 5 times the air rate. This considerable volumetric gas flow results in a large hydraulic load throughout the demetalling step that adversely impacts unit capacity, normal operation, and settler performance, and will cause flame stability difficulties in the burners of a downstream furnace or refinery flare, where the demetalling offgas is disposed of as fuel.

The design intent of the nitrogen addition system is to ensure that any gas mixture in or leaving the demetalling process is always above the upper flammable limit of the gas. The disadvantage of using nitrogen as an inert is that it does not lower the hydrogen/CO UFL of 74-75 vol % when the two gases are mixed. Calculations indicate that substituting natural gas (methane) for the nitrogen, the UFL of the mixture will be substantially lowered from 75 vol % for pure hydrogen, 74 vol% for pure carbon monoxide, ultimately to as low as 15 vol % for pure methane. This lowering of the UFL allows the oxygen content of the process gas stream to increase significantly and still remain non-flammable. This, in turn enables a significant reduction in the quantity of "dilution" gas that is required to render the oxygen-containing system non-flammable. The calculations show that, on the basis of an air feed rate of about 240 kg/hr [186 $Nm^3$/hr] introduced into the demetalling process, the dilution gas can be reduced from 1134 kg/hr [908 $Nm^3$/hr] to as low as 24 kg/hr [34 $Nm^3$/hr] if natural gas is substituted for nitrogen. This is the minimum amount of natural gas which results in an air/natural gas mixture and mixtures thereof with the hydrogen (and CO) containing gas mixture already present in the demetalling process, which, over the full range of possible mixing ratios, contains at least 15% flammables having a UFL of 15 vol %, and thus ensures that these are too rich to burn. While it is theoretically sufficient to provide this minimum amount of flammable diluent, we prefer to provide at least 1.5 times this minimum amount, preferably 2 times, more preferably 3 times, even more preferably 4 times and most preferably 5 times this minimum amount required to ensure the composition of the resulting gas mixture is above its upper flammability limit. Even if conservatively a safety factor of 5 may be applied, the dilution gas flow is still only 120 kg/hr [168 $Nm^3$/hr], which is only a fraction of what it needs to be with nitrogen as the diluent gas.

The additional advantage of using a flammable diluent is that the offgas from the demetalling section, once separated, may readily be used as a fuel to generate heat, which may be recovered for a useful purpose such as to generate steam.

CALCULATION METHODOLOGY

In our calculations we always assume pure hydrogen, and not a hydrogen/carbon monoxide mixture. Because it is only the UFL that matters, and the UFL of carbon monoxide is very close to the UFL of hydrogen, this is only a small error, and it is on the safe side.

To determine UFLs and percent "non-air" components, which is often somewhat misleadingly called the percent "flammables", in various gas mixtures with nitrogen addition, various compositions of a hydrogen/nitrogen mixture were examined and a UFL was determined for each. Then by assuming any desired air to inert nitrogen ratio, the amount of air that would be included with each hydrogen/nitrogen mixture can be calculated and the percent flammables can then be determined for each mixture. The data can then be plotted and the effect of various nitrogen to air ratios can be investigated.

For example, a gas containing 60 vol % hydrogen and 40 vol % nitrogen (air excluded):

Step 1: Determine UFL of gas

From literature it is known that the UFL of hydrogen is not changed by nitrogen dilution, so UFL=75 vol % (which is equivalent to an "air" content of 25 vol %)

This UFL should now be corrected for pressure and temperature as set out before.

Step 2: Determine percent "non-air".

Air enters process stream along with nitrogen based on set ratio.

We calculate for an operating curve wherein the air to nitrogen ratio=0.20 (vol)

For every 100 moles of hydrogen/nitrogen gas mixture, $H_2$=60 moles $N_2$=40 moles Air=8 moles (40×0.20)

$$\% \text{ non-air} = (\text{vol of gas} + \text{vol of inert}) / (\text{vol of gas} + \text{vol of inert} + \text{vol of air}) * 100$$

$$= (60 + 40)/(60 + 40 + 8) * 100$$

$$= 92.6 \text{ vol }\%$$

Step 3: Steps 1 and 2 are then repeated for all hydrogen/nitrogen gas combinations Step 4: Steps 2 and 3 are repeated for various air to nitrogen ratios.

Step 5: Plot all resultant data for analysis

The operating intent is to ensure that at no point does the percent "non-air", or flammables curve cross below the UFL curve for any gas combination.

Figure 1:
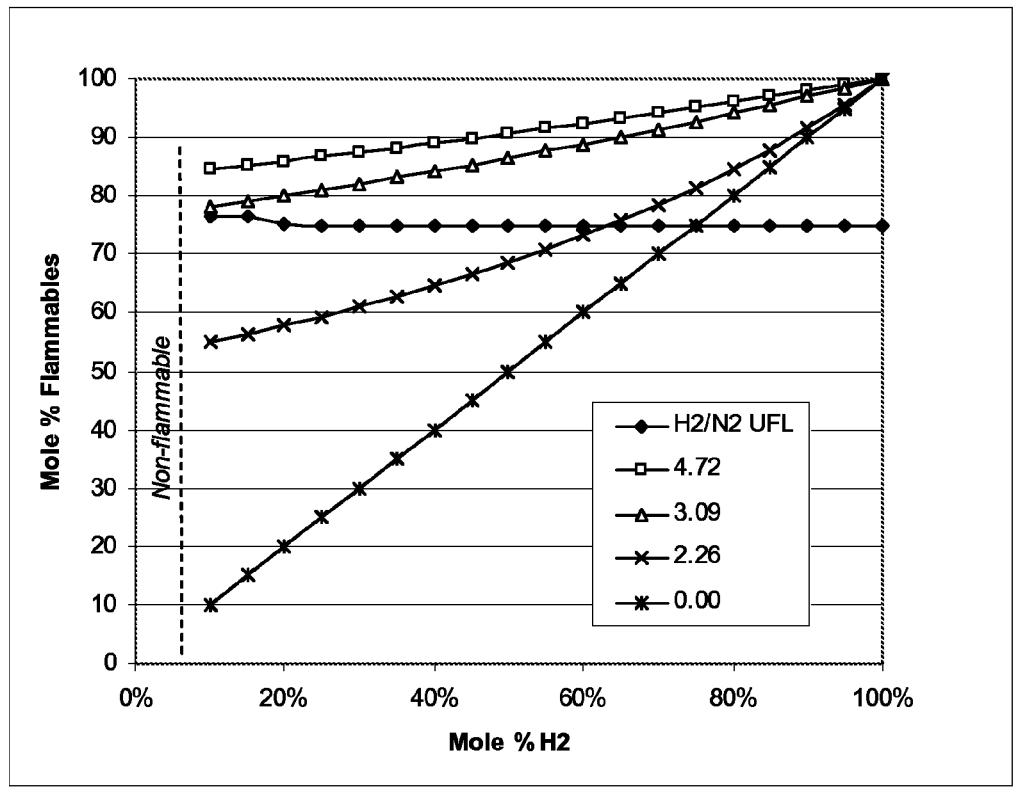
FIG. 1 shows the flammability diagram and operating curves of the prior art, when using nitrogen as the diluent.

This plot is shown in FIG. 1, which shows the Flammabilities with Nitrogen Addition (Hydrogen environment). The horizontal axis is the mole % hydrogen in the hydrogen/nitrogen mixture, the vertical axis is the % "non-air" or flammables in the gas mixture. The curve with the solid diamonds gives the UFL of the mixture, indicating that the gas mixture is flammable below that curve. The four other curves all start from the pure hydrogen point in the upper right corner, and show how the % non-air or flammables evolves as the nitrogen/air mixture is added. These operating curves thus cover the entire range of mixtures, from the point of no dilution at the right hand side down to almost all diluent and hardly any gas being diluted, at the left hand side of the graph. The four curves are for different mass ratios of nitrogen to air as indicated, with the lower of the four using pure air, i.e. no nitrogen dilution at all. These ratios are expressed as mass ratios for convenient use during commercial operations, where mass flow meters are preferably used. It can readily be calculated, and FIG. 1 indicates, that the $N_2$ to Air mass ratio needs to be about 3.09 in order to assure that under all circumstances the % non-air or flammables in the resulting gas mixture stays above the UFL curve. This is a border line situation, and assumes accurate measurements and flawless controls. In actual operation, the even higher nitrogen to air mass ratio of 4.72 is recommended, so that at all times and under all circumstances safe operation is maintained. This is about 1.5 times (152% of) the minimum amount required to ensure that the composition of the mixture formed is above its upper flammability limit.

For natural gas or pure methane as in our example, the methodology is similar, except a different calculation technique is required to determine the UFL of the hydrogen/methane mixture. The determination of the percent non-air or flammables in each mixture is accomplished as above, but now the air to natural gas ratio is used.

For example: a gas containing 60 vol % hydrogen and 40 vol % methane (air excluded)

Step 1: Determine UFL of gas

UFL=$1/(y_1/UFL_1+y_2/UFL_2)$; UFL of $H_2$=75.0, UFL of $CH_4$=15.0

UFL=1/(0.6/75.0+0.4/15.0)

UFL=28.8 vol % (equivalent to an "air" content of 71.2 vol %)

This UFL should now be corrected for pressure and temperature as set out before.

Step 2: Determine percent flammables (or "non-air")

Premise: Air enters process stream along with methane based on a set ratio.

We calculate for an operating curve wherein the air to methane ratio=1.20 (molar basis)

For every 100 moles of hydrogen/methane gas mixture, $H_2$=60 moles $CH_4$=40 moles Air=48 moles (40×1.20)

$$\% \text{ Flammables} = (\text{vol of flammable gases}) / (\text{vol of flammable gases} + \text{vol of air}) * 100$$

$$= (60 + 40)/(60 + 40 + 48) * 100$$

$$= 67.6 \text{ vol }\%$$

Step 3: Duplicate Steps 1 & 2 for all hydrogen/methane gas combinations

Step 4: Duplicate Steps 2 & 3 for various air to methane ratios

Step 5: Plot all resultant data for analysis (See FIG. 2)

The operating intent is to ensure that at no point does the percent flammables or "non-air" curve cross below the UFL curve for any gas combination.

Discussion of the calculated results is provided in the following sections.

The chart in FIG. 1 demonstrates the effect of various rates of nitrogen additions to the air stream that will become mixed with hydrogen, by comparing the percent flammables in the final gas mixture to the calculated UFL. The calculation methodology was as explained in the previous section. Targeting the top curve with the mass ratio of 4.72 and thus offering about a 50% higher dilution than minimally required, a flow of 1134 kg/hr [908 Nm³/hr] of nitrogen is required on the basis of a constant air rate of about 240 kg/hr [186 Nm³/hr] to ensure that, no matter what the hydrogen to nitrogen-air ratio might be, at no time would the oxidative demetalling section be operating below the UFL. This continues to be valid up until the nitrogen diluent addition is reduced so that the oxygen content is at a 5 vol % value in the nitrogen-air mixture (still using about 744 kg/hr [595 Nm³/hr] of nitrogen diluent). Any further reductions in nitrogen will result in some concentration that could be below the UFL of the mixture. Obviously, as seen on the chart, if no nitrogen is added, all concentrations of hydrogen in air from below 75% (UFL) and down to 5 vol % (LFL) would be flammable.

Figure 2:
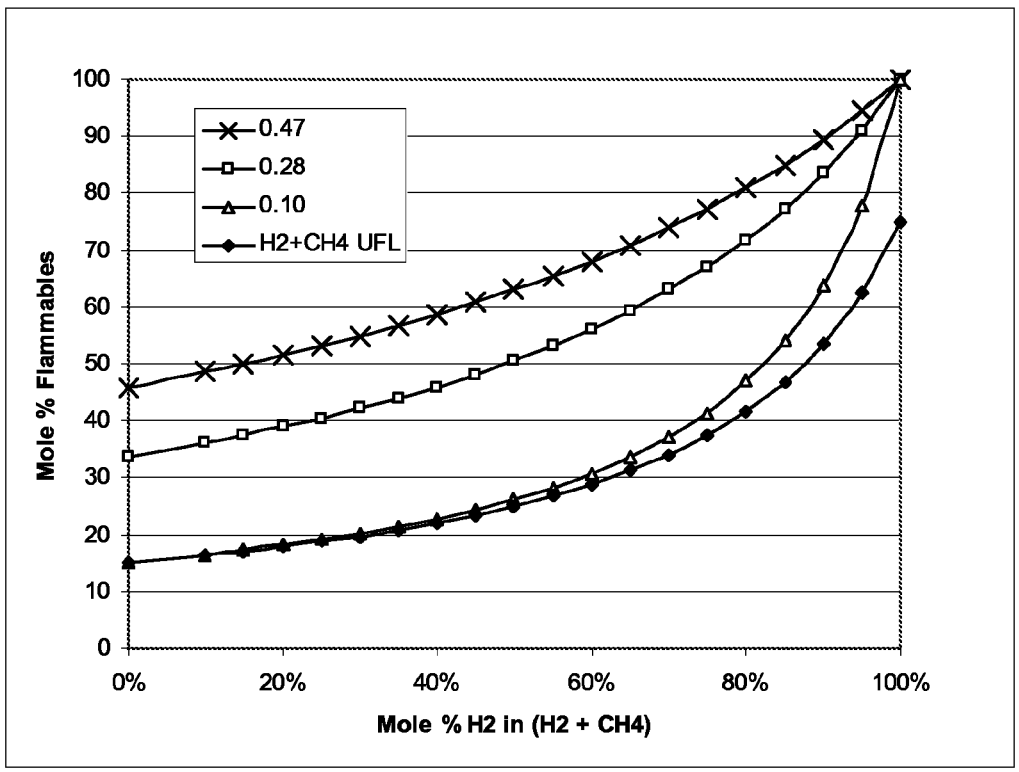
FIG. 2 shows the flammability diagram and operating curves according to the invention, when using methane as the diluent.

For our methane example, calculations were performed to determine the UFL of all methane to hydrogen ratios using the procedures as previously described. The results of the analysis are shown in FIG. 2. Three operating curves are provided, for three methane-to-air mass ratios, showing the percent non-air or flammables at various methane flow rates, along with the calculated UFLs. It follows the same format as FIG. 1, but now for methane addition. The horizontal axis is therefore the mole % of hydrogen in the hydrogen/methane mixture, and the vertical axis is the percent non-air or flammables in the resulting gas mixture. Again the curve with the solid diamonds shows the UFL, which now changes significantly with composition. The three other curves start again in the upper right corner with pure hydrogen, and move to the left with increasing air flow relative to the amount of hydrogen present. These three curves represent different methane to air mass ratios, with the values as indicated. The lowest curve of these three shows the critical lower minimum limit, indicating that a 0.10 mass ratio, or again on the basis of an air flow of 240 kg/hr [186 Nm³/hr], a flow of 24 kg/hr [34 Nm³/hr] of methane is required to ensure the composition of the resulting mixture is maintained above the UFL at all concentrations of hydrogen and the methane-air mixture. We prefer to provide a dilution that is above this minimum, such as at least 1.5 times, more preferably 2, 3, 4 and most preferably 5 times the minimum amount required. Conservatively thus, a recommendation to use 120 kg/hr [168 Nm³/hr] of methane represents a five fold safety factor above the minimum requirement.

It should now be clear that the main advantage of using methane is its low UFL of 15 vol % in air, compared to hydrogen or carbon monoxide. When mixed with hydrogen (and/or carbon monoxide), the combined UFL is significantly lowered based on the methane to hydrogen volume ratio. With pure hydrogen, the air concentration must be no higher than 25 vol %, for the resulting mixture to be above the UFL. With pure methane, the air concentration can be as high as 85 vol % and the mixture is still not flammable. Since for ease of operation, the injected air flow is basically set at a constant rate in the demetalling section, by applying the principle of the invention considerably less dilution gas is required while offering a much lower UFL.

Figure 3:
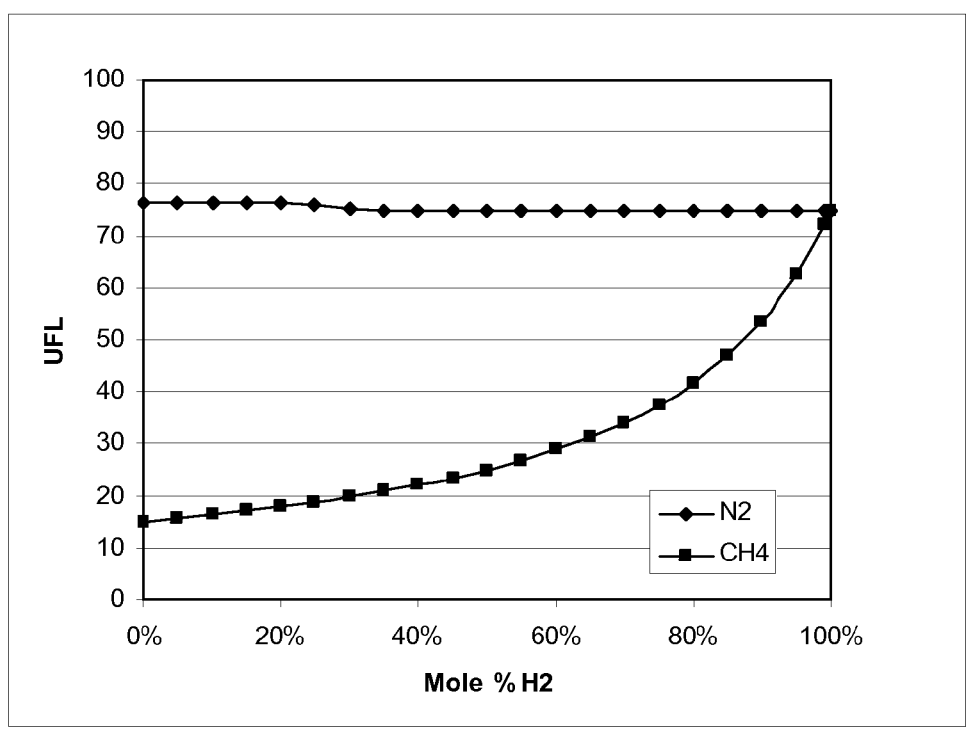
FIG. 3 compares the Upper Flammability Limits of mixtures of hydrogen with nitrogen and with methane.

FIG. 3 illustrates the difference between the UFLs for the nitrogen/hydrogen [$N_2$] and the methane/hydrogen [$CH_4$] alternatives. The horizontal axis shows the mole % of hydrogen in the gas mixture (air excluded), and the vertical axis gives the Upper Flammability Limit, expressed as percent non-air or flammables in air. Since the intent is to ensure that the gas mixture in the demetalling section is always operating above the UFL no matter what operating scenario is assumed, the methane dilution option gives a much larger safe window of operation with a substantial reduction in the gas volume flowing through the process, as compared to the nitrogen dilution option.

Methane is only an example. Within the principle of the inventive concept other flammable diluents, or mixtures thereof may be chosen, and the methodology as explained above may be readily adapted to the selection of another flammable diluent or diluent mixture.

As an alternative to employing the calculation methodology presented here, one may make use of the CHEMSAFE database, i.e. "CHEMSAFE database for safety characteristics", STN International (online), edited by a.o. the "Bundesanstalt für Materialforschung und -prüffung (BAM)", Berlin, the "Physikalisch-Technische Bundesanstalt (PTB), the "Braunschweig and Deutsche Gesellschaft für Chemische Apparatewesen, and the Chemische Technik und Biotechnologie (DECHEMA) e.V., Frankfurt am Main.

For even better refinement, in particular if inert gases are present, one may make use of the information published by Rennhack, R.: Experimentelle Bestimmung der Explosionsgrenzen der Brenngase CO, $CH_4$, und $H_2$ mit den Inerten $N_2$, $CO_2$, $H_2O$, Argon und Helium in Luft oder Sauerstoff im Temperaturbereich 20 bis 400° C. bei Umgebungsdruck. Universität-GH Paderborn, FB 10 Verfahrenstechnik; (Version 2 of Jul. 23, 1992)

The advantages attainable by use of the invention will depend on the particular embodiments selected, but may include a significant reduction in the hydraulic load of the demetalling section;

improved operation of the three phase settler, resulting in a potentially reduced acid usage in the oxidative demetalling section (often formic and/or acetic acids are used here);

substantial reduction in the consumption of nitrogen, which is often charged at a premium incremental cost;

a reduction in natural gas or other fuel consumption in the downstream furnace where the offgas is burned, which without use of the invention would be needed for heating the large nitrogen stream up to flame temperature;

more stable operation of the burners in downstream furnaces and/or flare where the offgas from the demetalling section is disposed of as fuel; and possible reduction in electrical power consumption, due to a reduced pressure drop in the demetalling section, because the process pressure at the point of injection of the air/diluent and acid/water streams is reduced.

By the use of the invention, a further advantage may be realised downstream from the demetalling step, more particularly in the systems that are handling the gas phase that is separated from the organic liquid. In one embodiment, this gas phase may be disposed of in a collective blowdown system, and the blowdown gasses may either be combusted at the top of a flare stack, or recovered by recompression and introduction into a fuel gas system. Because the composition of such combined offgasses may vary widely over time, and at times contain significant amounts of nitrogen from equipment purging, it is not uncommon in such systems to bleed in extra natural gas or flammable gasses, such that the combustion of these gasses is not impaired. We have found that, by replacing nitrogen as the gas diluent in demetalling by natural gas, and hence a flammable gas according to the invention, the amount of gas needed for bleed into the blowdown system could be reduced significantly, in our case with as much as 230 kg/hr (500 lbs/hr) of natural gas. As this reduction of the natural gas bleed in resulted in a net reduction of the site energy consumption of more than 3 MWh (about 250 MBtu/day), and a net $CO_2$ emission reduction of almost 5000 tons per year.

The demetalled product from the process of the invention may be stored in a tank before being processed further. As the product contains aldehydes, it is preferable to avoid contact of the product with the atmosphere, such that the formation of acids by the oxidation of aldehyde is minimised. The tanks for such demetalled hydroformylation product may therefore be blanketed with an oxygen-free vapor phase. Because aldehydes have a characteristic and rather strong odour, it is preferred to avoid routing any of the vents from such blanketed tankage to atmosphere. We therefore prefer to recover such vent gasses from tankage in the site blowdown drum or system, and/or recover them through a vapour compression recovery system that recompresses such vent gasses up to a pressure allowing them to be recovered as fuel gas, preferably via the site fuel gas system. In order to avoid impairment of the combustion of the vent gasses from these tanks, we prefer to use a flammable gas for the tank blanketing, more preferably natural gas. We have found that there is significant benefit in monitoring and optimising the usage of flammable gas and the vapour recovery system operation, as we noticed that this lead to a reduction in energy consumption of the order of 1.8 MWh (155 MBtu/day) and a reduction in $CO_2$ emission of almost 3000 tons per year.

Having now fully described this invention, it will be appreciated by those skilled in the art that the invention can be performed within a wide range of parameters within what is claimed, without departing from the spirit and scope of the invention.

What is claimed is:

1. A process for demetalling the organic reaction product of a homogeneous metal-catalysed reaction of an organic liquid, which includes the step of introducing an oxygen-containing gas into the organic reaction product to oxidise metal residues in the product, the oxidation being performed in the presence of a separate gas phase comprising flammable components, wherein said process further includes the step of introducing a flammable gas as a diluent into the separate gas phase to increase the concentration of flammables in the separate gas phase and ensure that the composition of the separate gas phase is above its upper flammability limit.

2. The process according to claim 1, wherein the amount of diluent introduced is at least 1.5 times the minimum amount required to ensure that the composition of the separate gas phase is above its upper flammability limit.

3. The process according to claim 1 wherein the flammable gas is mixed with the oxygen-containing gas and the resulting mixture is then introduced into the reaction product to effect oxidation of the metal residues therein, the composition of the mixture of the oxygen-containing gas with the flammable diluent being above its upper flammability limit.

4. The process according to claim 1 wherein the flammable gas comprises a hydrocarbon.

5. The process according to claim 4 wherein the hydrocarbon is methane.

6. The process according to claim 1 wherein the flammable gas is natural gas.

7. The process according to claim 1 wherein the oxygen-containing gas is air.

8. The process according to claim 1 wherein the homogeneous metal-catalysed reaction comprises a hydroformylation reaction.

9. A process comprising hydroformylating an olefin into an aldehyde by use of a homogeneous metal catalyst, which comprises demetalling the hydroformylation product by the process according to claim 1.

10. The process according to claim 9, which further comprises a step of oxidising the aldehyde into an acid.

11. The process according to claim 10, which further comprises a step of esterifying the acid with an alcohol to produce an ester.

12. The process according to claim 9, which further comprises a step of hydrogenating the aldehyde into an alcohol.

13. The process according to claim 12, which further comprises a step of esterifying the alcohol with an acid or an anhydride to produce an ester.

14. The process according to claim 13 wherein the ester is a benzoate, a phthalate or a trimellitate, further comprising hydrogenating the ester to produce the corresponding cyclohexane mono-, di- or tri-ester.

* * * * *